United States Patent [19]

Hagen

[11] 4,447,641
[45] May 8, 1984

[54] PROCESS FOR PREPARATION OF ALPHA, BETA-UNSATURATED ESTERS USING AMS-1B BOROSILICATE CRYSTALLINE MOLECULAR SIEVE

[75] Inventor: Gary P. Hagen, Glen Ellyn, Ill.

[73] Assignee: Standard Oil Company (Indiana), Chicago, Ill.

[21] Appl. No.: 401,549

[22] Filed: Jul. 26, 1982

[51] Int. Cl.$^3$ .......................................... C07C 67/343
[52] U.S. Cl. .................... 560/211; 560/104; 560/122; 560/128; 260/410.9 R
[58] Field of Search ............... 560/210, 212, 211, 104, 560/128, 122; 562/599; 423/277; 260/410.9 R

[56] References Cited

U.S. PATENT DOCUMENTS

| | | | |
|---|---|---|---|
| 3,014,958 | 12/1961 | Koch et al. | 560/210 |
| 3,089,901 | 5/1963 | Vitcha et al. | 560/210 |
| 4,118,588 | 10/1978 | Fouquet et al. | 560/210 |
| 4,269,813 | 5/1981 | Klotz | 252/432 |

FOREIGN PATENT DOCUMENTS 48-31081 9/1973 Japan.

OTHER PUBLICATIONS

Kirk–Othmer *Encyclopedia: of Chemical Technology*, 2nd Ed. Interscience Publ., vol. 7 at p. 393 and vol. 13 at p. 339.
Hara, Nobuyoshi et al., *Chemical Abstracts*, vol. 80, (1974), #26,725s.

*Primary Examiner*—Natalie Trousof
*Assistant Examiner*—L. Hendriksen
*Attorney, Agent, or Firm*—William C. Clarke; William T. McClain; William H. Magidson

[57]  ABSTRACT

Alpha, beta-unsaturated esters are prepared by reaction between dimethylformal and carboxylic acid compounds of the formula RCH$_2$COOR′ wherein R is a member of the class consisting of —H, -alkyl, -aryl, -aralky, -cycloalkyl, and -alkylaryl radicals, and R′ is selected from the group consisting of —H and —CH$_3$ radicals in the presence of AMS-1B borosilicate crystalline molecular sieve catalyst under reaction conditions.

21 Claims, No Drawings

PROCESS FOR PREPARATION OF ALPHA, BETA-UNSATURATED ESTERS USING AMS-1B BOROSILICATE CRYSTALLINE MOLECULAR SIEVE

BACKGROUND OF THE INVENTION

This invention relates to the production of alpha, beta-unsaturated methyl esters by reaction between dimethylformal and carboxylic acid compounds of the formula $RCH_2COOR'$ wherein R is a member of the class consisting of —H, -alkyl, -aryl, -aralkyl, -cycloalkyl, and -alkylaryl radicals. Where R is not hydrogen, the number of carbon atoms in R is preferably from 1 to 18. R' is selected from the group consisting of —H and —$CH_3$ radicals.

It is well-known that methyl alpha-methacrylate and methyl acrylate can be prepared by reacting formaldehyde with a suitable reactant, i.e., methyl propionate and methyl acetate, in the presence of a suitable catalyst. This invention is directed to an in situ process for synthesis of alpha, beta-unsaturated methyl esters, e.g., methyl alpha-methacrylate (and methyl acrylate) from propionic acid (or acetic acid) and methyl esters of such acids dimethylformal, i.e., formaldehyde in the form of its dimethyl acetal of the formula $CH_3OCH_2OCH_3$. The process requires the presence of a catalyst comprising a borosilicate crystalline molecular sieve, designated as AMS-1B, having the following composition in terms of mole ratios of oxides:

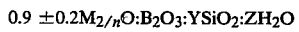

$$0.9 \pm 0.2 M_{2/n}O:B_2O_3:YSiO_2:ZH_2O$$

wherein M is at least one cation, n is the valence of the cation, Y is a value within the range of 4 to about 600, and Z is a value within the range of 0 to about 160, and providing a specific X-ray diffraction pattern.

Unsaturated acids, such as methacrylic and acrylic acids, acrylonitrile and the esters of such acids, such as methyl alpha-methacrylate, are widely used for the production of corresponding polymers, resins and the like. Various process and catalysts have been proposed for the conversion of alkanoic acids, such as propionic acid, and various forms of formaldehyde to the corresponding unsaturated monocarboxylic acids, e.g., methacrylic acid, by an aldol-type reaction. Generally, the reaction of the acid and formaldehyde takes place in the vapor or gas phase while in the presence of a basic or acidic catalyst.

Various catalysts have been proposed for such reactions. For example, Vitcha, et al., *I&EC Product Research and Development*, 5, No. 1 (March, 1966) pp. 50–53, propose a vapor phase reaction of acetic acid and fomaldehyde employing catalysts comprising alkali and alkaline earth metal aluminosilicates, silica gel, alumina and the like. U.S. Pat. No. 2,734,074 teaches the preparation of acrylic ester by formaldehyde condensation with a lower alkyl ester in the presence of a dehydration catalyst comprising lead acetate suspended on silica gel. U.S. Pat. No. 2,821,543 teaches a similar preparation using basic metal compounds such as basic reacting salts or oxides of metals, i.e., manganese oxide, deposited upon a suitable carrier such as activated alumina or activated silica. U.S. Pat. No. 3,051,747 describes the preparation of acrylic acids by reacting an alkanoic acid and formaldehyde in the presence of a catalyst comprising an alkali metal salt of the alkanoic acid supported on alumina. The same reaction is also promoted by catalysts which include alkali metal or alkaline earth metal aluminosilicates, silica gel or alumina. Catalysts of this kind are described in U.S. Pat. No. 3,247,248 which teaches a process for the reaction of formaldehyde and acetic acid or propionic acid in the presence of a natural or synthetic aluminosilicate catalyst that may include alkali or alkaline earth metals, such as the aluminosilicates of sodium, potassium, rubidium, magnesium, calcium, strontium or barium. In addition, the use of silica gel in combination with an alkali metal or alkaline earth metal hydroxide as a catalyst for the reaction is described. U.S. Pat. No. 3,933,888 teaches the preparation of unsaturated acids, the esters and nitriles of such unsaturated acids wherein alkanoic acids, esters of such acids and alkyl nitriles are reacted with formaldehyde in the presence of a basic catalyst comprising pyrogenic silica. The pyrogenic silica is taught as especially effective when treated with activating agents which provide basic sites on the pyrogenic silica catalyst support, such as organic bases, inorganic bases of Groups IA, IIA and IIIB of the Periodic Table, particularly the alkali metal hydroxides such as potassium hydroxide and cesium hydroxide. The addition of a compound of a metal as an activating agent is taught as increasing the effectiveness of the catalyst.

Other processes and catalysts have been proposed for the preparation of methacrylic acid and esters. U.S. Pat. No. 3,089,898 teaches a process and catalyst for preparation of methyl acrylate which comprises contacting vapor mixtures of methyl acetate and formaldehyde with aluminosilicate catalysts, particularly alkaline earth metal zeolites, alkali metal zeolites and zeolites of certain heavy metals such as manganese, cobalt, zinc, cadmium and lead. Aqueous and alcoholic sources of formaldehyde are taught as useful. U.S. Pat. No. 3,089,899 teaches preparation of methyl methacrylate which comprises contacting vapor mixtures of methyl propionate and formaldehyde with zeolite catalysts, particularly certain synthetic zeolites, especially the aluminosilicates of Group IIA of the Periodic Table, such as magnesium, calcium, strontium and barium aluminosilicates, and manganous aluminosilicates. Aqueous of alcoholic formaldehyde or anhydrous paraformaldehyde can be used. U.S. Pat. No. 3,089,900 teaches preparation of methyl methacrylate using a catalyst consisting of potassium hydroxide impregnated on silica gel. G.B. Pat. No. 1,107,234 teaches a similar process using potassium, rubidium or cesium hydroxide on silica gel as catalyst. U.S. Pat. No. 3,089,901 teaches use of alkali metal metaborates on silica gel and alkali metal tetraborates on silica gel as catalysts. U.S. Pat. No. 3,089,902 teaches alkali metal silicate on silica gel as catalyst.

Accordingly, a number of processes using basic metal catalysts have been taught heretofore. Other process using basic metal compounds on silica gel catalysts are taught in U.S. Pat. Nos. 3,100,795; 3,247,248; 3,534,087; 3,670,016; 3,840,587; 3,840,588. But, although an alkali-treated silica gel improves the activity of the formaldehyde with regard to the desired reaction, at the same time, as is well-known, formaldehyde has a tendency to undergo undesirable side reactions owing to its high reactivity in alkaline media.

Processes to minimize or to avoid the aforesaid undesirable side reactions which formaldehyde undergoes in alkaline media have been taught. U.S. Pat. No. 3,535,371 teaches use of a niobium oxide catalyst on alumina. U.S. Pat. No. 3,845,106 teaches use of an unmodified silica gel. G.B. Pat. No. 1,491,183 teaches use of methylal instead of formaldehyde with a metal oxide catalyst, preferably $Al_2O_3$. U.S. Pat. No. 4,085,143 teaches use of a catalyst comprising silica gel and a salt or an oxide of a metal selected from the group consisting of tantalum, titanium, niobium, and zirconium with an acid anhydride and formaldehyde. Boric acid deposited an alumina is also taught as a catalyst. U.S. Pat. No. 4,118,588 teaches a process and catalyst for preparing methacrylic acid and methyl methacrylate which comprises reacting, respectively, propionic acid and methyl propionate with dimethoxymethane in the presence of catalysts based on phosphates and/or silicates of magnesium, aluminum, zirconium, thorium and/or titanium and in the presence of water. Boric acid and/or urea can also be present. Preferably, the catalysts are modified with alkali metal and/or alkaline earth metal carboxylates and/or alkali metal compounds and/or alkaline earth metal compounds which yield carboxylates under the reaction conditions. Suitable modifiers are the carboxylates, oxides and hydroxides of lithium, sodium, potassium, magnesium and calcium as well as those of beryllium, strontium, rubidium, cesium and barium.

However, the processes and catalysts taught heretofore suffer from disadvantages which are greatly minimized in the process of the present invention. For example, the processes as described in Vitcha, *I&EC*, op. cit. p. 50, are inferior to the present invented process in that conversion of formaldehyde is low when acid concentration is low. Vitcha indicates that as the ratio of acetic to formaldehyde decreases, the competitive reaction of formaldehyde with itself to form polymers predominates, to result in lower conversion and yield. Other examples can be cited. U.S. Pat. No. 3,051,747 indicates that the major product of the process is not an unsaturated compound but a symmetric ketone. The process described in U.S. Pat. No. 3,247,248 is also inferior to the process of the present invention. Yield percent based on formaldehyde taught by U.S. Pat. No. 3,247,248 with 5:1 ratios of acid to formaldehyde is between 20 and 40 percent.

Quite unexpectedly, it has been found that a catalyst comprising AMS-1B borosilicate crystalline molecular sieve having the following composition in terms of mole ratios of oxides:

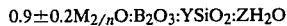

$$0.9\pm 0.2 M_{2/n}O:B_2O_3:YSiO_2:ZH_2O$$

wherein M is at least one cation, n is the valence of the cation, Y is a value within the range of 4 to about 600, and Z is a value within the range of 0 to about 160, and providing a specific X-ray diffraction pattern, performs in a much superior manner for the present process with respect to conversion and selectivity relative to conventional catalysts. Whereas previously taught catalyst formulations require a basic metal on silica or alumina substrates, the catalyst of the instant invented process is a borosilicate crystalline molecular sieve catalyst. Yield and selectivity are also improved over previously taught catalysts. The improved process has several unexpected results. Whereas previously taught processes result in low formaldehyde-based yields of methyl alpha-methacrylate or methyl acrylate when the ratio of acid to formaldehyde is low, such as 1:1, the preferred acid:dimethylformal ratio for the process of the present invention is 0.5:1 to 20:1, preferably 1:1, with consequent economic advantage. Also, in previously taught processes, substantial amounts of acid often are formed from the ester from ester-cleavage side reactions. Even when the reaction is carried out in the presence of excess alcohol, the formation of acid via cleavage is not easily suppressed.

The process and catalyst of the instant invention circumvent the ester-cleavage mechanism by utilizing an acid:dimethylformal mechanism. In preparation of methyl alpha-methacrylate, the major products of the reaction, methyl propionate and methyl methacrylate, are easily separated by conventional methods. The methyl propionate can be reached with formaldehyde under suitable process conditions to prepare methyl alpha-methacrylate, and, alternatively, along with unesterified propionic acid, is recycled to the reactor. In this way, methyl alpha-methacrylate is conveniently synthesized in situ directly from propionic acid and without the need for a separate esterification section within the overall process. In addition, the present invention is with the use of a dry derivative of formaldehyde, dimethylformal.

An object of the present invention is to provide a process for making unsaturated methyl esters from saturated carboxylic acids and dimethylformal. A further object is to provide a process for making methyl acrylate. A further object is to provide a process for making methyl alpha-methacrylate. Other objects will appear hereinafter.

SUMMARY OF THE INVENTION

Disclosed is a process for production of alpha, beta-unsaturated methyl esters by reaction between the acetal of formaldehyde, dimethylformal, and carboxylic acid compounds of the formula $RCH_2COOR'$, wherein R is a member of the class consisting of —H, -alkyl, -aryl, -aralkyl, -cycloalkyl, and -alkylaryl radicals, the number of carbon atoms in R being preferably from 1 to 18 when R is not hydrogen, R' being selected from the group consisting of —H and —$CH_3$ radicals, in the presence of AMS-1B borosilicate crystalline molecular sieve catalyst under reaction conditions wherein the acid compound:acetal mole ratio is from about 0.5:1 to 20:1 at a temperature within the range of from about 250° C. to about 430° C.

DETAILS OF THE INVENTION

The process of the instant invention relates to a process for production of alpha, beta-unsaturated methyl esters by reaction of dimethylformal and carboxylic acid compounds of the formula $RCH_2COOR'$ wherein R is a member of the class consisting of —H, -alkyl, -aryl, -aralkyl, -cycloalkyl, and -alkylaryl radicals, the number of carbon atoms in R being preferably from 1 to 18 when R is not hydrogen, R' is selected from the group consisting of —H and —$CH_3$ radicals, in the presence of AMS-1B borosilicate crystalline molecular sieve catalyst. In preparation of methyl alpha-methacrylate and methyl acrylate (from propionic acid and acetic acid), yield is increased over previously taught process and production of by-products is minimized. Recycle of the methyl propionate and methyl acetate resulting from the preparation of methyl alpha-methacrylate and methyl acrylate further increases yield of the desired products. The general method requires the presence of AMS-1B borosilicate crystalline molecular sieve catalyst. Dimethylformal is reacted with propionic acid (or acetic acid) in the gas phase at a temperature within the range of from about 250° C. to about 430° C.

The present invention relates to a process using a synthetic crystalline molecular sieve material, a crystalline borosilicate, as a catalyst. The family of such crystalline borosilicate materials, which are identified as AMS-1B borosilicates, and which are taught in commonly-assigned U.S. Pat. No. 4,269,813, incorporated herein by reference, has a particular X-ray diffraction pattern. Such crystalline borosilicate can generally be characterized, in terms of the mole ratios of oxides, as follows in Equation I:

$$0.9 \pm 0.2 M_{2/n}O:B_2O_3:YSiO_2:ZH_2O$$

wherein M is at least one cation, n is the valence of the cation, Y is between 4 and about 600, and Z representing the water present in such material is between 0 and about 160, or more.

In another instance, the claimed crystalline borosilicate can be represented in terms of mole ratios of oxides for the crystalline material not yet activated or calcined at high temperatures as follows in Equation II:

$$0.9 \pm 0.2 [WR_2O + (1-W)M_{2/n}O]:B_2O_3:YSiO_2:ZH_2O$$

wherein R is an alkylammonium cation, M is at least one cation, n is the valence of the cation, Y is a value between 4 and 600, Z is a value between 0 and about 160, and W is a value greater than 0 and less than 1.

In Equation I, M can represent an alkali-metal cation, an alkaline-earth-metal cation, an ammonium cation, an alkylammonium cation, a hydrogen cation, a catalytically-active-metal cation, or mixtures thereof. In Equation II, M can represent an alkali-metal cation, an alkaline-earth-metal cation, an ammonium cation, a hydrogen cation, a catalytically-active-metal cation, or mixtures thereof.

Advantageously, the value for Y falls within the range of 4 to about 500. Suitably, Y is 4 to about 300; preferably, about 50 to about 160; and more preferably, about 80 to about 120.

Suitably, Z is within the range of 0 to about 40.

The original cation M in the above formulations can be replaced in accordance with techniques well-known in the art, at least in part by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically active, especially for hydrocarbon conversion. These materials include hydrogen, natural occurring rare earth metals of Group IIIB, lanthanum, aluminum, metals of Groups IA, i.e., sodium, potassium, lithium, etc.; IIA, i.e., calcium, strontium, barium, etc., and VIII, i.e., iron, cobalt, nickel, etc. of the Periodic Table of Elements found in the 46th edition of the *Handbook of Chemistry and Physics* published by the Chemical Rubber Company; noble metals, manganese, and other catalytically active materials and metals known to the art. Rare earth metals, lanthanum, sodium and hydrogen are considered especially useful. The catalytically active components, separately or in any combination, can be present anywhere from about 0.05 to about 25 weight percent of the AMS-1B crystalline borosilicate. The form wherein hydrogen replaces the original cation M and n is 1 in the above formulations is designated HAMS-1B. The hydrogen form of the AMS-1B crystalline borosilicate catalyst imparts an acid character to the catalyst to improve yields of methyl alpha-methacrylate and methyl acrylate. Molecular sieves containing divalent and trivalent cations are generally recognized to impart acidic character to molecular sieves but the hydrogen ion is considered to impart more acidic character.

Embodiments of such borosilicate composition useful in the process of the instant invented process provide an X-ray diffraction pattern comprising the following X-ray diffraction lines:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | wherein the assigned strengths correspond to the following values of relative peak heights:

| Assigned Strength | Relative Peak Height |
|---|---|
| VW | less than 10 |
| W | 10-19 |
| M | 20-39 |
| MS | 40-70 |
| VS | greater than 70 |

A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formations of said borosilicate, said reaction conditions comprising a reaction temperature within the range of about 25° C. to about 300° C., a pressure of at least the vapor pressure of water at the reaction temperature, and a reaction time that is sufficient to effect crystallization. The hydrogen form can be obtained by ion exchange.

The AMS-1B crystalline borosilicate useful in this invention can be in an unsupported form for use either in a fixed bed or fluidized bed reactor. The AMS-1B crystalline borosilicate can be combined with active or inactive materials, synthetic or naturally-occurring zeolites, as well as inorganic or organic materials which would be useful for binding the borosilicate. Well-known materials include silica, silicaalumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. Catalytic compositions can contain about 0.1 wt. % to about 100 wt. % crystalline borosilicate material and preferably contain about 10 wt. % to about 80 wt. % of such material and most preferably contain about 30 wt. % to about 65 wt. % of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

It has been found that borosilicate catalysts prepared by the above method are effective in catalyzing the reaction of carboxylic acids, particularly propionic acid and acetic acid, and an acetal, i.e., dimethylformal, under anhydrous conditions wherein the acid:dimethylformal ratio is from about 0.5:1 to about 20:1 at a temperature within the range of from about 250° C. to about 430° C. and contact time is from about 0.1 to about 20 seconds.

It is essential for the process and catalyst of the instant invention that water in the acid compound-acetal feed and in the reactor under operating conditions be maintained at low levels, preferably no greater than a maximum of 8% by weight of the combined weight of the acid compound-acetal feed, more preferably no greater than 4% by weight. Since water is produced as a by-product of the reaction, the reaction can be self-deactivating to the extent that higher conversions of the acid compound-dimethylformal reactants cause higher gas phase concentrations of water in the catalyst bed, thus requiring an increased operating temperature which in turn decreases selectivity to the alpha, beta-unsaturated methyl ester.

The alpha carbon of the reactant acid of the formula $RCH_2COOH$ and its methyl ester is required to possess at least two hydrogen atoms. When R is not hydrogen suitable carboxylic acids and esters preferably contain from 1 to 18 carbon atoms in addition to the $-CH_2COOH$ or $-CH_2COOCH_3$ moiety. Examples of acids and esters are acetic acid, propionic acid, n-butyric acid, n-valeric acid, isovaleric acid, n-caproic acid, n-heptanoic acid, capric and lauric acids, phenylacetic acid, gamma-phenylbutyric acid, 3-methylcyclopentylacetic acid, and the methyl esters thereof.

In the example, the novel process of the present invention is carried out to synthesize methyl alpha-methacrylate from propionic acid and dimethylformal. The instant invented process is useful in synthesis of methyl acrylate by the vapor phase reaction of acetic acid and dimethylformal. The instant invented process is also useful in synthesizing unsaturated monocarboxylic methyl esters from methyl esters of monocarboxylic acids of the formula $RCH_2COOR'$ wherein R and R' are as previously defined.

The instant invented process, as exemplified, is a single step in situ process for the synthesis of methyl alpha-methacrylate which is catalyzed effectively by a borosilicate crystalline molecular sieve catalyst as described herein.

The invented process involves the condensation of dimethylformal with propionic acid and methyl propionate, separately and in a mixture, to yield methyl alpha-methacrylate.

The reaction occurs at atmospheric pressure in the gas phase when the reactants are passed through the catalyst in the presence of a nitrogen carrier gas at a temperature of 250° C. to about 430° C., preferably 250° C.-330° C. Above 400° C. significant amounts of 3-pentanone (3-P), a known thermal degradation product of propionic acid, are formed, as well as some gaseous by-products. Reactant pressures of from 0.5 to 10 atmospheres can be used. A broad range of reactant ratios may be successfully used for this process. For example, when propionic acid and dimethylformal, in mole ratios varying from 0.5:1 to 20:1 propionic acid:available dimethylformal, are allowed to react at a temperature of about 300° C., yields of methyl alpha-methacrylate obtained can be up to about 11%, based on propionic acid. Total yields of methyl alpha-methacrylate and methyl propionate obtained can be as high as about 75%, based on propionic acid. Methyl propionate is extractable by suitable means, such as distillation with use of an inhibitor, and recycled for additional methyl alpha-methacrylate.

Recycle of the methyl propionate from the reaction of propionic acid and dimethylformal is preferably wherein the mole ratio of methyl propionate: dimethylformal is within the range of from about 20:1 to 1:1 but more preferably about 10:1. In operation, the methyl propionate and unreacted propionic acid are recycled to the reactor with make-up propionic acid added to obtain a 0.5:1 to 20:1 mole ratio, preferably a 1:1 ratio, acid:dimethylformal mole ratio. Ratio of methyl propionate:dimethylformal can vary in a feedstream comprising propionic acid which results from recycle operation due to process conditions and the acid:dimethylformal molar ratio.

In recycle operation wherein carboxylic acid compounds of formula $RCH_2COOR'$ are reacted with dimethylformal, mole ratio of carboxylic acids of formula $RCH_2COOH$ to dimethylformaldehyde can be from 0.5 to 20:1, mole ratio of carboxylic acid ester of formula $RCH_2COOR'$ to dimethylformal can be from 20:1 to 1:1, and preferred mole ratio is 10:1:2, carboxylic acid ester:acid:dimethylformal, upon an additive basis.

Liquid hourly space velocity (LHSV) measured in terms of volume of liquid per volume of catalyst per hour $(V_1V_c^{-1}hr^{-1})$, basis a constant carrier gas rate, is from about 0.05 to 20.0, preferably from about 0.1 to about 10.0. A LHSV less than about 0.05 results in nonselective decomposition of reactants. A LHSV above 20 results in low conversion of reactants.

Yield calculations can be based upon propionic acid, methyl propionate or dimethylformal. For example, propionic acid-based yields are calculated as follows:

$$\frac{\text{Moles Methyl Alpha-Methacrylate of Product}}{\text{Moles Propionic Acid in Feed}} \times 100 = \text{Yield}$$

Dimethylformal-based yields are calculated as follows:

$$\frac{\text{Moles Methyl Alpha-Methacrylate of Product}}{\text{Moles Dimethylformal in Feed}} \times 100 = \text{Yield}$$

Propionic acid selectivity is calculated as follows:

$$\frac{\text{Moles Methyl Alpha-Methacrylate of Product}}{\text{Moles Propionic Acid Reacted}} \times 100$$
$$= \text{Propionic Acid Selectivity}$$

Dimethylformal selectivity is calculated similarly.

The instant invention accordingly comprises a process for the preparation of alpha, beta-unsaturated methyl esters by reaction between dimethylformal and carboxylic acid compounds of the formula RCH$_2$COOR' wherein R is a member of the class consisting of —H, -alkyl, -aryl, -aralkyl, -cycloalkyl, and -alkylaryl radicals and R' is selected from the group consisting of —H radicals and -CH$_3$ radicals, in the presence of AMS-1B borosilicate crystalline molecular sieve catalyst under reaction conditions wherein the acid compound:dimethylformal mole ratio is from about 0.5:1 to 20:1 at a temperature within the range of from about 250° C. to about 430° C.

The instant invention also comprises the above said process wherein said carboxylic acid compounds of the formula RCH$_2$COOR' are recycled and comprise carboxylic acids of the formula RCH$_2$COOH, methyl esters of the formula RCH$_2$COOCH$_3$ and mixtures thereof wherein the acid:dimethylformal mole ratio is from about 0.5:1 to 20:1 and the methyl ester RCH$_2$COOCH$_3$:dimethylformal mole ratio is within the range of from about 20:1 to about 1:1.

The invention will be illustrated by reference to the following specific example.

EXAMPLE I

The quartz reactor consisted of a quartz tube fitted with a thermocouple through the center of the tube to measure and control temperature. Inlets were provided at the top of the reactor for the carrier gas stream and feed materials. The catalyst bed was positioned in the reactor by an inert support material. Product was removed at the bottom of the quartz tube. Heat was supplied by an electric tube furnace.

A 5.7 ml portion of a 15.3 ml solution containing propionic acid (7.0 ml, 6.95 g, 0.0938 mole) and dimethylformal (8.3 ml, 7.4 g, 0.0968 mole) was prepared. Molar ratio was 1:1. The solution was drawn into a syringe which was then attached to a syringe pump and connected to a septum mounted near the top of the reactor with a long stainless steel needle. The reactor had been loaded with 1.00 g of alumina-supported HAMS-1B (50 wt. % HAMS-1B and 50 wt. % alumina), the hydrogen ion form of a catalyst prepared from AMS-1B, and the catalyst bed was brought to 301° C. under a stream of nitrogen gas flowing at a rate of 8.6 ml/min. A 5.7 ml portion of the solution was allowed to pass into the reactor at a rate of 0.108 ml per minute. Contact time was 2.7 seconds. The pale yellow product was collected in a receiver and analyzed by quantitative G.C. (gas chromatographic) analysis (Carbowax 20M column). It was found to contain methyl propionate (0.02248 mole, 64.41% yield) methanol (0.00335 mole, 9.3% yield), propionic acid (0.00370 mole), and alpha-methyl methacrylate (0.00375 mole, 10.74% yield), based on propionic acid. Selectivities were: alpha-methyl methacrylate 12.01%, methyl propionate 72.05%, methanol 10.38%. Conversion based on propionic acid was 89.40%. Total selectivity to useful products, alpha-methyl methacrylate and methyl propionate (which can be recycled) was 84.1%.

EXAMPLE II

In the procedure of Example I, propionic and dimethylformal were reacted in the presence of alumina-supported HAMS-1B catalyst (50 wt. % HAMS-1B and 50 wt % alumina) to prepare methyl alpha-methacrylate. Mole ratios of propionic acid to dimethylformal were 10:1, 5:1, and 1:2. Catalyst temperature, LHSV and nitrogen carrier gas rates were maintained at about constant values and contact times were similar. All reactions were carried out with 1.0 g of HAMS-1B catalyst.

In the reaction of propionic acid with dimethylformal, the highest yield of methyl alpha-methacrylate, based on propionic acid, was obtained with a 1:1 mole ratio of propionic acid and dimethylformal exemplified in Example I. As the mole ratio of propionic acid to dimethylformal decreased from 10:1 to 5:1, the yield of methyl alpha-methacrylate increased correspondingly. Even at a ratio of 1:2, using a catalyst with 4.19 hours of prior use, yield of methyl alpha-methacrylate was 2.3% based on propionic acid. Process data and results are given in Table I. Data from Example I are included for comparison.

TABLE I

Synthesis of Methyl Alpha-Methacrylate With Propionic Acid and Dimethylformal

| Run No. 5528 | 142 | 200 | 148 | Example I |
|---|---|---|---|---|
| Process Data | | | | |
| Catalyst Temp. °C. | 303 | 302 | 304 | 301 |
| Contact Time (sec) | 3.63 | 3.66 | 3.72 | 2.7 |
| Mole Ratio (PA:DF) | 10:1 | 5:1 | 1:2 | 1:1 |
| Catalyst Prior Use-Hours | 1.49 | 0 | 4.19 | 0 |
| Results | | | | |
| % Conversion PA | 21.9 | 38.8 | 96.3 | 89.4 |
| % Yield - Me Meth | 1.4 | 2.6 | 2.3 | 10.7 |
| Me Prop | 17.8 | 33.9 | 76.7 | 64.4 |
| % Selectivity | | | | |
| PA to Me Meth | 6.3 | 6.7 | 2.3 | 12.1 |
| PA to Me Prop | 80.9 | 87.2 | 79.6 | 72.05 |

Notes: Process conditions on Runs No. 5528-142, -200, -148 were:
Syringe Pump Rate (ml/min)  0.0774
LHSV (V$_1$V$_c^{-1}$hr$^{-1}$)  1.27
N$_2$ Carrier Rate (ml/min)  5.9–6.5
PA is propionic acid.
DF is dimethylformal.
Me Meth is methyl alpha-methacrylate.
Me Prop is methyl propionate.
Yields are based on propionic acid.

EXAMPLE III

In the procedure of Example I, methyl propionate and dimethylformal were reacted in the presence of alumina-supported HAMS-1B catalyst (50 wt % HAMS-1B and 50 wt % alumina) to prepare methyl alpha-methacrylate. Mole ratios of methyl propionate to dimethylformal were 10:1, 5:1 and 1:1.

Catalyst temperature, LHSV and nitrogen carrier gas rates were maintained at about constant values and contact times were similar. All reactions were carried out with 1.0 g of HAMS-1B catalyst.

In the reaction of methyl propionate with dimethylformal, the highest yield of methyl alpha-methacrylate, based on dimethylformal, was obtained with a 10:1 mole ratio of methyl propionate:dimethylformal. As the ratio of methyl propionate to dimethylformal decreased, the yield of methyl alpha-methacrylate decreased correspondingly. Even at a ratio of 10:1, using a catalyst with 3.9 hours of prior use, yield of methyl alpha-methacrylate was 29.9%, based on dimethylformal. Process data and results are given in Table II.

TABLE II

Synthesis of Methyl Alpha-Methacrylate With Methyl Propionate and Dimethylformal

| Run No. 5543 | 126 | 128 | 130 |
|---|---|---|---|
| Process Data | | | |
| Catalyst Temp. °C. | 296 | 300 | 302 |
| Contact Time (sec) | 4.36 | 4.30 | 4.07 |
| Mole Ratio (MP:DF) | 10:1 | 5:1 | 1:1 |
| Catalyst Prior Use-Hours | 3.0 | 0 | 0 |
| Results | | | |
| % Conversion MP | 19.3 | 22.0 | 58.4 |
| % Yield - Me Meth (DF) | 29.9 | 19.8 | 2.6 |
| PA (MP) | 8.6 | 8.7 | 8.2 |
| % Selectivity | | | |
| MP to PA | 44.8 | 39.8 | 5.4 |
| MP to Me Meth | 15.5 | 18.0 | .5 |

Notes: Process conditions were:
  Syringe Pump Rate (ml/min)   0.0774
  LHSV ($V_1V_c^{-1}hr^{-1}$)   1.27
  $N_2$ Carrier Rate (ml/min)   6.1–6.6

MP is methyl propionate.
DF is dimethylformal.
Me Meth is methyl alpha-methacrylate.
PA is propionic acid.
Me Meth (DF) yield is based on dimethylformal.
PA (MP) yield is based on methyl propionate.

What is claimed is:

1. A process for the preparation of alpha, beta-unsaturated methyl esters by reaction between dimethylformal and carboxylic acid compounds of the formula $RCH_2COOR'$ wherein R is a member of the class consisting of —H, -alkyl, -aryl, -aralkyl, -cycloalkyl, and -alkylaryl radicals and R' is selected from the group consisting of —H radicals and —$CH_3$ radicals, in the presence of AMS-1B borosilicate crystalline molecular sieve catalyst under reaction conditions wherein the acid compound:dimethylformal mole ratio is from about 0.5:1 to 20:1 at a temperature within the range of from about 250° C. to about 430° C.

2. The process of claim 1 wherein said AMS-1B is the hydrogen form AMS-1B.

3. The process of claim 2 wherein hydrogen of hydrogen form AMS-1B is replaced by a member of the group consisting of rare earth metals, lanthanum and sodium.

4. The process of claim 1 wherein R is selected from the group consisting of -alkyl, -aryl, -aralkyl, -cycloalkyl, and -alkylaryl radicals and contains from 1 to 18 carbon atoms.

5. The process of claim 1 wherein R' is —H and said acid compound is propionic acid.

6. The process of claim 1 wherein R' is —H, said acid compound is propionic acid and said alpha, beta-unsaturated methyl ester is methyl -methacrylate.

7. The process of claim 1 wherein R' is —H and said acid compound is acetic acid.

8. The process of claim 1 wherein R' is —H, said acid compound is acetic acid and said alpha, beta-unsaturated methyl ester is methyl acrylate.

9. The process of claim 1 wherein R' is —H and said acid compound:dimethylformal mole ratio is 1:1.

10. The process of claim 1 wherein R' is —$CH_3$, said acid compound is methyl propionate and said alpha, beta-unsaturated methyl ester is methyl -methacrylate.

11. The process of claim 1 wherein R' is —$CH_3$, said acid compound is methyl acetate and said alpha, beta-unsaturated methyl ester is methyl acrylate.

12. The process of claim 1 wherein R' is —$CH_3$ and said acid compound:dimethylformal mole ratio is 10:1.

13. The process of claim 1 wherein said carboxylic acid compounds of the formula $RCH_2COOR'$ are recycled and comprise carboxylic acids of the formula $RCH_2COOH$, methyl esters of the formula $RCH_2COOCH_3$ and mixtures thereof wherein the acid:dimethylformal mole ratio is from about 0.5:1 to about 20:1 and the methyl ester $RCH_2COOCH_3$:dimethylformal mole ratio is within the range of from about 20:1 to about 1:1.

14. The process of claim 13 wherein said acid:dimethylformal mole ratio is 1:1, said methyl ester $RCH_2COOCH_3$:dimethylformal mole ratio is 10:1 and said carboxylic acid ester:acid:dimethylformal mole ratio is 10:1:2.

15. The process of claim 1 wherein said temperature is within the range of from about 250° C. to about 330° C.

16. The process of claim 1 wherein water content of said acid compound and said dimethylformal is no greater than 8% by weight.

17. The process of claim 1 wherein water content of said acid compound and said dimethylformal is no greater than 4% by weight.

18. The process of claim 1 wherein said AMS-1B borosilicate crystalline molecular sieve composition is incorporated within an alumina or silica-alumina matrix.

19. The process of claim 1 wherein said AMS-1B borosilicate crystalline content in said matrix ranges from about 10 to 80 wt. %.

20. The process of claim 1 wherein said AMS-1B borosilicate crystalline content in said matrix ranges from about 30 to 65 wt. %.

21. The process of claim 1 wherein said AMS-1B crystalline molecular sieve composition is unsupported.

* * * * *